United States Patent
Ingledew et al.

(10) Patent No.: US 9,266,072 B2
(45) Date of Patent: *Feb. 23, 2016

(54) DEVICES AND METHODS FOR IMPROVED DELIVERY OF VOLATILE LIQUIDS

(75) Inventors: Natalie Ingledew, Hull (GB); Loic Marouse, Margny-les-Compiegne (FR); Steve Walsh, Frimley (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 153 days.

This patent is subject to a terminal disclaimer.

(21) Appl. No.: 13/806,206

(22) PCT Filed: Jun. 28, 2011

(86) PCT No.: PCT/GB2011/051221
§ 371 (c)(1),
(2), (4) Date: Feb. 26, 2013

(87) PCT Pub. No.: WO2012/001404

PCT Pub. Date: Jan. 5, 2012

(65) Prior Publication Data
US 2013/0152790 A1 Jun. 20, 2013

(30) Foreign Application Priority Data

Jul. 1, 2010 (GB) .................................. 1011076.5

(51) Int. Cl.
*B01F 3/04* (2006.01)
*A01M 1/20* (2006.01)
(Continued)

(52) U.S. Cl.
CPC .......... *B01F 3/04049* (2013.01); *A01M 1/2033* (2013.01); *A01M 1/2044* (2013.01);
(Continued)

(58) Field of Classification Search
CPC ....................................................... B01F 3/04
USPC ..................................................... 261/78.2
See application file for complete search history.

(56) References Cited

U.S. PATENT DOCUMENTS 2,612,432 A  9/1952  Boddy
2,814,081 A  11/1957 Stevenson
(Continued)

FOREIGN PATENT DOCUMENTS

EP  0092359 A  10/1983
EP  1076014 A2  2/2001
(Continued)

OTHER PUBLICATIONS

GB Search Report for GB1011076.5 dated Nov. 1, 2010.
(Continued)

*Primary Examiner* — Duane Smith
*Assistant Examiner* — Adam W Bergfelder
(74) *Attorney, Agent, or Firm* — Norris McLaughlin & Marcus PA

(57) ABSTRACT

An emanation device is described which comprises: a replaceable refill of liquid containing one or more active materials wherein the active material comprises at least one of: a fragrance; an insecticide; a fungicide; a pesticide; a sanitizing material; and/or a pharmaceutical; wherein the refill comprises a sealed reservoir containing said volatile liquid and a porous wick which extends from the interior of the reservoir to the exterior thereof; and wherein the device comprises: an air pump; a fluid conduit in fluid communication with the air pump such that, in use, air pumped by the pump will flow through the fluid conduit; a nozzle located at the end of the fluid conduit remote from the air pump; a ejector constriction provided in the fluid conduit adjacent or substantially adjacent the nozzle; a liquid conduit provided adjacent the ejector constriction and in fluid communication with the fluid conduit at one end thereof, and open at the other end to receive liquid therein; characterized in that the liquid conduit is located within the porous wick.

22 Claims, 2 Drawing Sheets

(51) Int. Cl.
  *A61L 9/12* (2006.01)
  *A61L 9/14* (2006.01)
(52) U.S. Cl.
  CPC ............... *A61L 9/125* (2013.01); *A61L 9/127* (2013.01); *A61L 9/14* (2013.01); *A61L 2209/11* (2013.01); *A61L 2209/111* (2013.01); *A61L 2209/133* (2013.01)

(56) References Cited

U.S. PATENT DOCUMENTS

| | | |
|---|---|---|
| 3,796,541 A | 3/1974 | Gentil |
| 3,872,280 A | 3/1975 | Van Dalen |
| 4,166,087 A | 8/1979 | Cline et al. |
| 4,200,229 A | 4/1980 | Spector |
| 4,346,059 A | 8/1982 | Spector |
| 4,370,300 A | 1/1983 | Mori et al. |
| 4,950,457 A | 8/1990 | Weick |
| 2002/0130146 A1* | 9/2002 | Borut et al. .............. 222/645 |
| 2002/0168301 A1 | 11/2002 | Channer |
| 2005/0178345 A1 | 8/2005 | Crapser |
| 2005/0199742 A1 | 9/2005 | Maat |
| 2006/0022064 A1 | 2/2006 | Triplett et al. |
| 2006/0045359 A1 | 3/2006 | Chen et al. |
| 2006/0175425 A1 | 8/2006 | McGee et al. |
| 2007/0204387 A1 | 9/2007 | Cornelius et al. |
| 2007/0217771 A1 | 9/2007 | Granger et al. |
| 2008/0149665 A1 | 6/2008 | Hafer et al. |
| 2008/0251598 A1 | 10/2008 | Ross |
| 2010/0187324 A1 | 7/2010 | Feygin et al. |
| 2010/0243754 A1 | 9/2010 | Harris |

FOREIGN PATENT DOCUMENTS

| | | |
|---|---|---|
| EP | 1714662 A1 | 10/2006 |
| EP | 1849485 A1 | 10/2007 |
| FR | 2556242 A1 | 6/1985 |
| GB | 2233230 A | 1/1991 |
| GB | 2357973 A | 7/2001 |
| GB | 2480906 A | 12/2011 |
| GB | 2481635 A | 1/2012 |
| WO | 9607484 A1 | 3/1996 |
| WO | 9949904 A1 | 10/1999 |
| WO | 03003826 A2 | 1/2003 |
| WO | 03103387 A2 | 12/2003 |
| WO | 2004002542 A1 | 1/2004 |
| WO | 2004094071 A1 | 11/2004 |
| WO | 2004096299 A1 | 11/2004 |
| WO | 2006004891 A1 | 1/2006 |
| WO | 2006045359 A1 | 5/2006 |
| WO | 2007109504 A2 | 9/2007 |
| WO | 2008034977 A2 | 3/2008 |
| WO | 2011098641 A1 | 8/2011 |
| WO | 2011161462 A1 | 12/2011 |
| WO | 2012001404 A1 | 1/2012 |
| WO | 2012001405 A1 | 1/2012 |
| WO | 2012059771 A1 | 5/2012 |

OTHER PUBLICATIONS

International Search Report for PCT/GB2011/051221 dated Sep. 8, 2011.

Written Opinion of the International Searching Authority for PCT/GB2011/051221 dated Sep. 8, 2011.

Notification Concerning Transmittal of International Preliminary Report on Patentability for PCT/GB2011/051221 dated Jan. 17, 2013.

International Preliminary Report on Patentability or PCT/GB2011/051221 dated Jan. 8, 2013.

* cited by examiner

DEVICES AND METHODS FOR IMPROVED DELIVERY OF VOLATILE LIQUIDS

This is an application filed under 35 USC 371 of PCT/GB2011/051221.

FIELD OF THE INVENTION

The present invention relates to devices and methods for improved airborne delivery of liquids, particularly volatile liquids, containing one or more active materials wherein the active material comprises at least one of: a fragrance; an insecticide; a fungicide; a pesticide; a sanitising material; and/or a pharmaceutical.

BACKGROUND

Liquids, an particularly volatile liquids, containing one or more active materials wherein the active material comprises at least one of: a fragrance; an insecticide; a fungicide; a pesticide; a sanitising material; and/or a pharmaceutical are delivered within the domestic environment via a variety of mechanisms. Devices are available with heaters disposed therein to increase the rate of emanation from a surface saturated with the liquid, such a surface could be a wick saturated with a fragranced liquid and the heater is located adjacent the wick surface and nearby a chimney to heat the liquid on the wick surface and cause it to more readily evaporate and disseminate into the surrounding environment through the chimney.

Alternatively such liquids can be loaded in an aerosol canister, the canister holds the liquid under pressure and when the canister valve is opened the liquid is forced out. The liquid is provided with a propellant which evaporates inside the canister to maintain an even pressure and, outside the canister, assist with the mechanical break up of the liquid by evaporating rapidly. Suitable propellants include volatile hydrocarbons such as propane, butane or isobutane.

Aerosols generally provide a satisfactory spray performance but since they require manual operation by a user, they are not considered to be particularly convenient for routine use. Automatic aerosol activation devices exist for operation with metered dose aerosols. These devices are operable to periodically actuate the aerosol to cause a dose of the liquid to be sprayed.

Whilst the automation of the device overcomes the problem of manual operation of a canister, the use of aerosols containing such propellants is becoming increasingly less desirable since these volatile hydrocarbons carry the disadvantage of being flammable, the rising cost of oil is rendering them increasingly expensive and they also carry the further disadvantage of being an atmospheric source of carbon which is deemed to not be environmentally sensitive.

In the field of air freshening it is generally preferred to use a fragranced liquid/air freshening liquids comprising several components. These components often possess different volatilities which can lead to emission problems. The effect of fractionation can be particularly pronounced for powered emanation devices using a heater to effect emanation such as a plug-in emanation device or the like.

In such device a build-up phenomenon can occur in which an accumulation of volatile liquid components with the lowest comparative volatilities can occur leading to an undesirable non-uniform emanation profile for the liquid. This phenomenon can produce an olfactory sensation wherein the fragrance character changes over the course of emanation of a quantity of the fragranced volatile liquid such that the 'high notes' of a fragrance are the first to be evaporated when the wicking material is first exposed to the fragranced liquid, and the 'low notes' are evaporated thereafter.

Accordingly, it is an object of the present invention to provide a device that is capable of addressing the abovementioned performance drawbacks and other drawbacks that will be appreciated by a person skilled in the art.

SUMMARY OF INVENTION

According to a first aspect of the present invention there is provided therefore an emanation device comprising:

a replaceable refill of liquid containing one or more active materials wherein the active material comprises at least one of: a fragrance; an insecticide; a fungicide; a pesticide; a sanitising material; and/or a pharmaceutical; wherein the refill comprises a sealed reservoir containing said liquid and a porous wick which extends from the interior of the reservoir to the exterior thereof;

and wherein the device comprises:

an air pump;

a fluid conduit in fluid communication with the air pump such that, in use, air pumped by the pump will flow through the fluid conduit;

a nozzle located at the end of the fluid conduit remote from the air pump;

a ejector constriction provided in the fluid conduit adjacent or substantially adjacent the nozzle;

a liquid conduit provided adjacent the ejector constriction and in fluid communication with the fluid conduit at one end thereof, and open at the other end to receive liquid therein;

characterised in that the liquid conduit is located within the porous wick.

According to a second aspect of the present invention there is provided therefore an emanation device comprising:

two or more replaceable refills of liquid containing one or more active materials wherein the active material comprises at least one of: a fragrance; an insecticide; a fungicide; a pesticide; a sanitising material; and/or a pharmaceutical; wherein the refills each comprise a sealed reservoir containing said liquid and a porous wick which extends from the interior of the reservoir to the exterior thereof; and wherein the device comprises:

one or more air pumps;

two or more fluid conduits corresponding to the number of replaceable refills, wherein said fluid conduits are in fluid communication with the or each air pump such that, in use, air pumped by the pump(s) will flow through the fluid conduits;

a nozzle located at the end of each fluid conduit remote from the air pump(s);

a ejector constriction provided in each fluid conduit adjacent or substantially adjacent the nozzle;

a liquid conduit provided adjacent each ejector constriction and in fluid communication with the respective fluid conduit at one end thereof, and open at the other end to receive liquid therein;

characterised in that each liquid conduit is located within respective porous wicks of said two or more replaceable refills.

Devices according to either the first of second aspect of the present invention have been found to be particularly advantageous as they are capable of spraying the liquid at a uniform consistency thus avoiding the drawbacks of fractionation and/or build-up phenomena.

The liquid conduit is preferably made from a rigid or substantially rigid material such as a metal, alloy or plastics material, this may be advantageous in allowing said conduit to penetrate the wick. The open end of the liquid conduit may be provided with a sharpened point or the like to assist with penetration of the wick.

The liquid conduit is preferably provided in a length that is less than the length of the wick, in other words the liquid conduit preferably extends from the fluid conduit to a length that will not contact a base interior surface of the refill reservoir. In this arrangement the transport of the liquid from the reservoir of the refill to and past the nozzle of the device is achieved by the liquid being transported by capillary action into the wick and then transported via suction imposed by the ejector constriction acting in cooperation with the pumped air up into the liquid conduit and out past the nozzle. This arrangement is preferred as it is easier for a user of the device of the present invention to insert the liquid conduit partially into the wick rather than insert it along the entire length of the wick. This arrangement is also preferred as the wick is more efficient at ensuring all of the liquid in the reservoir is taken up into the wick since it is less susceptible to not contacting pooled liquid in the lower portions of the reservoir.

The refill is preferably a commercially available refill of liquid such as that sold under the brand AIRWICK® for use with a mains electric fragrance diffuser sold under the same brand. The refill may be made from a reservoir that is partially or completely transparent thus allowing a user to monitor the liquid level therein. Preferably the reservoir is made from glass or a substantially rigid plastics material. The reservoir is preferably sealed with a plug having an aperture therethrough, and the aperture is preferably sized to correspond to the diameter or cross-section of the wick thus securely holding the wick in a fixed position whilst substantially maintaining a liquid seal to substantially or completely prevent the leaking of liquid from the reservoir. The refill is preferably provided with a removable cap that surrounds the plug and the protruding wick to protect the wick and prevent emanation of the liquid from the wick until emanation of the liquid is required.

The wick is preferably made from a wrapped fibrous material, such as wrapped cellulose or the like. The wick may be made from any porous material wherein said porous material sufficiently malleable to permit the liquid conduit to be at least partially inserted therein.

The wick is preferably sized to extend from a base of reservoir to protrude through the plug or a reservoir seal to extend thereabove.

A further advantage of the present invention over typical devices used for emanating liquids from a wicked replaceable refill, such as a mains electrical plug in diffuser, is that since heat is not used to drive the emanation of the liquid, there will be no unsightly discolouration of the wick.

The refill may be provided with a releasably attachable cap wherein an uppermost section of an upper portion of the cap is formed from a weaker material than the remainder of the cap, whereby the liquid conduit may be able to relatively easily pierce through the weaker material in order to locate the liquid conduit within the porous wick. The cap may be arranged such that the cap is provided with a base portion that contains means configured to engage with cap closure means provided on the refill and the cap may be provided further with an upper portion arranged to extend away from the base portion to accommodate the wick therewithin.

Preferably the weaker material at the uppermost section of the upper portion is provided by an aperture covered by one or more pierceable films, such as a thin plastics membrane and/ or a metal foil and/or metallised foil or the like. Preferably however, for the conservation of manufacturing costs a single pierceable film is provided.

Alternatively the weaker material at the uppermost section of the upper portion may be provided by the cap being formed of thinner material at the uppermost section relative to the remainder of the cap such that the thinner material is easily pierceable.

Alternatively the cap may be formed from at least two different materials that are bonded together, the base portion being formed from a first material that is a substantially non-pierceable material and all of the upper portion, or at least the uppermost section of the upper portion, is formed of a second material that is a pierceable material.

Preferably the uppermost section of the upper portion is provided with guide means in a central portion thereof to assist in the liquid conduit piercing the cap, and subsequently the wick, appropriately. The guide means may be provided in the form of a tapered recess that is configured to cooperate with a correspondingly shaped tapered means surrounding the liquid conduit.

The device may be provided with refill securing means which are configured to retain the refill in a substantially fixed position relative to the device to ensure the safe operation of the device during use and prevent the likelihood of damage to the liquid conduit.

The air pump is preferably configured to pump air through the fluid conduit within a range of substantially 0.4-1.0 liters/ min, and preferably substantially 0.6-0.8 liters/min.

The ejector constriction is preferably provided in the form of a nozzle insert, even more preferably said nozzle insert substantially fills the nozzle and permits the flow of liquid therefrom.

The nozzle insert is preferably configured to extend from or adjacent the nozzle along the interior of the fluid conduit and may be provided at a rearward portion thereof that is remote from the nozzle with a channel. The channel may be inwardly tapered toward a forward portion thereof to, in use, further lower the pressure and increase the speed of air pumped therethrough, forward of the inward taper may be provided a ejector constriction portion. Forward from said ejector constriction portion may be provided an expansion chamber. The liquid conduit preferably connects to the fluid conduit in the ejector constriction portion to be in fluid communication with the fluid conduit and/or the nozzle insert such that, in use, the decrease in pressure at the connection draws liquid up the liquid conduit into the fluid conduit and/or nozzle insert before being carried by the pumped air flow out of the nozzle or nozzle insert into the environment surrounding the device.

Alternatively the ejector constriction can be formed integrally with the fluid conduit adjacent the nozzle. As a further alternative the ejector constriction can be formed integrally with the nozzle.

The nozzle or nozzle insert may be provided with one or more break-up bars and/or swirl chambers in order to improve the mechanical break up of the liquid being sprayed therefrom in use.

The device is preferably provided with a controller that is configured to control the air pump to control the spraying of liquid from the device. Preferably the controller is provided with a timer to permit the controller to instruct the pump to operate for periods defined by the controller. The device may be provided with user input means to allow a user to instruct the controller how long to spray for and/or how often to spray for and/or the spray rate of the device.

The device may be provided with a sensor means which is connected to the controller wherein said sensor means is configured to detect a characteristic in the environment surrounding the device. The controller would preferably be operative to analyse an input from the sensor means and control the air pump to spray a determined amount of liquid.

Preferably the sensor means is provided by at least one motion sensor means and/or at least one odour sensor means.

The motion sensor means may be provided in the form of at least one of: an infrared (IR) sensor; a laser sensor; and a sound sensor. The IR sensor, which is preferably a passive IR sensor, may be operable to detect radiation in the infrared spectrum, thus be capable of detecting the presence of a person or an animal within the vicinity of the device. The laser sensor may be operable to emit one or more laser beams and be adapted to detect when an object breaks the one or more beams by moving across the beam(s), thus indicating the presence of a person or an animal within the vicinity of the device. The sound sensor may be operable to detect sound within the vicinity of the device and, preferably, once the detected sound exceeds a predefined level this is indicative of movement within the vicinity of the device.

The odour sensor means may be provided by a MOS sensor or the like and may be operable to detect common household odours (and the chemicals which constitute) these malodours. For example: kitchen malodour; bathroom malodour; tobacco smoke; pet odours; mould and/or mildew; body odour; fish; onions; garbage; fragrance from other products (such as detergents, polishes, cleaning products etc). To facilitate such detection the odour sensor means may be operable to detect at least some of the following chemical components: amines and nitrogen compounds; acids and/or sulphur compounds, such as mercaptans, thioacids, thioesters, sulfides, phenols and skatole.

The device of any of the above-mentioned aspects may be provided with an indicator wherein said indicator is operable to indicate to a user what function the device is currently performing. The indicator may be operable to provide a visual indication and/or provide an audible indication.

Preferably the indicator is configured to provide a visual indication by emitting light from one or more light sources, preferably one or more LEDs.

The one or more light sources may be adapted to emit a different colour of light to indicate the current function the device is performing. Additionally or alternatively, the one or more light sources may blink or flash to indicate the current function the device is performing.

Alternatively or additionally, the device may be operable to visually indicate the function currently being performed by the device via a screen. The screen may be an LCD screen that is adapted to provide a message to a user, for instance such messages could include "ON", "DISPENSING", "RESTING", "NORMAL MODE", "DETECTING MODE", "BOOST MODE", "OFF".

The device may be power by mains-supplied electricity and/or be battery powered and/or be powered by solar cells located on the device. Most preferably the device is battery powered however to improve the portability thereof. Indeed battery powered is preferred as the use of such power is consider to be particularly advantageous over typical devices used for emanating liquids from a wicked replaceable refill, such as a mains electrical plug in diffuser, is that the device does not need to be located adjacent an electrical plug socket nor within an acceptable distance of the socket such that there can be a electrical power cord between the device and plug socket, thus providing true portability.

According to a third aspect of the present invention there is provided therefore a method of emanating a liquid containing one or more active materials wherein the active material comprises at least one of: a fragrance; an insecticide; a fungicide; a pesticide; a sanitising material; wherein said method comprises the steps of:
at least partially inserting a liquid conduit of a device according to either the first or second aspect of the present invention into a wick of a refill of liquid containing one or more active materials;
causing an air pump to pump air into a fluid conduit and out of a nozzle past a ejector constriction such that liquid is sucked from the wick into the liquid conduit and out of the nozzle into the environment surrounding the device.

According to a fourth aspect of the present invention there is provided therefore a fragrance emanation device for use with a replaceable refill of liquid containing one or more active materials wherein the active material comprises at least one fragrance; wherein the refill comprises a sealed reservoir containing said liquid and a porous wick which extends from the interior of the reservoir to the exterior thereof wherein the device comprises:
an air pump;
a fluid conduit in fluid communication with the air pump such that, in use, air pumped by the pump will flow through the fluid conduit;
a nozzle located at the end of the fluid conduit remote from the air pump;
a ejector constriction provided in the fluid conduit adjacent or substantially adjacent the nozzle;
a liquid conduit provided adjacent the ejector constriction and in fluid communication with the fluid conduit at one end thereof, and open at the other end to receive liquid therein;
characterised in that the liquid conduit is located within the porous wick.

According to a fifth aspect of the present invention there is provided therefore a fragrance emanation device for use with two or more replaceable refills of liquid each containing one or more active materials wherein the active material comprises at least one fragrance; wherein the refills each comprise a sealed reservoir containing said liquid and a porous wick which extends from the interior of the reservoir to the exterior thereof wherein the device comprises:
one or more air pumps;
two or more fluid conduits corresponding to the number of replaceable refills, wherein said fluid conduits are in fluid communication with the or each air pump such that, in use, air pumped by the pump(s) will flow through the fluid conduits;
a nozzle located at the end of each fluid conduit remote from the air pump(s);
a ejector constriction provided in each fluid conduit adjacent or substantially adjacent the nozzle;
a liquid conduit provided adjacent each ejector constriction and in fluid communication with the respective fluid conduit at one end thereof, and open at the other end to receive liquid therein;
characterised in that each liquid conduit is located within respective porous wicks of said two or more replaceable refills.

Any of the features described herein may be combined with any of the above aspects in any combination.

BRIEF DESCRIPTION OF THE DRAWINGS

Embodiments of the invention will now be described, by way of example only, with reference to the following drawing in which.

DESCRIPTION OF AN EMBODIMENT

Figure 1:
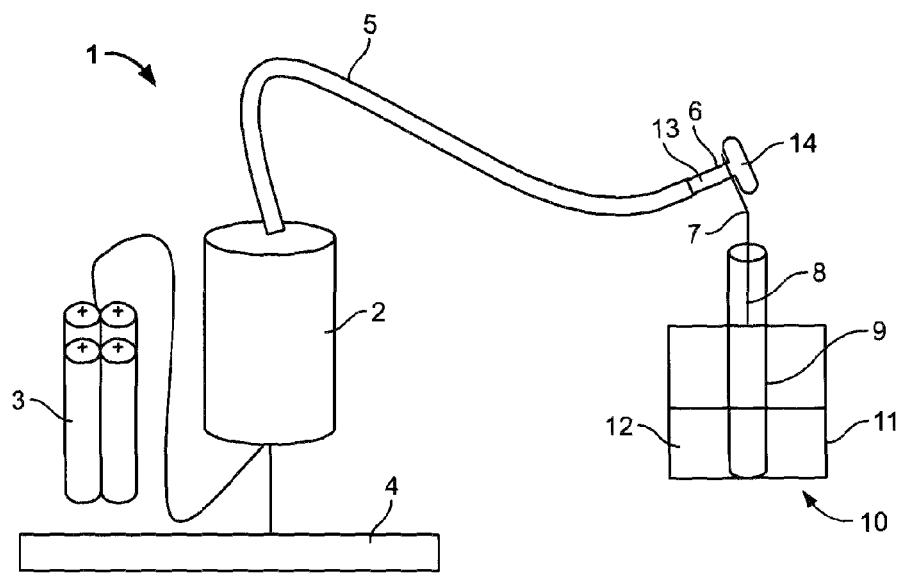
FIG. 1 illustrates an exploded view of the principal components of a device according to the present invention.
Figure 2:
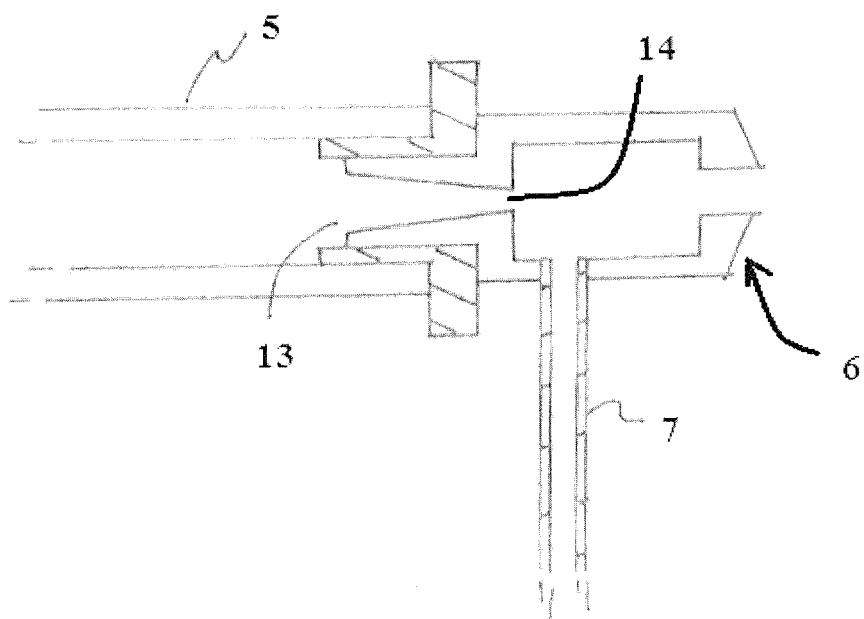

FIG. 1 illustrates an exploded view of the principal components of the device 1 according to the present invention. The device 1 consists of an air pump 2 which is powered by batteries 3 and controlled by a controller 4 provided in the form of a PCB with suitable components attached thereto to facilitate control of the air pump 2. FIG. 2 illustrates a cross sectional view of a nozzle insert 6.

The air pump 2 is shown in fluid communication with a fluid conduit 5 such that air pumped by the pump 5 is pumped into the fluid conduit 5. The pumped air passes along the fluid conduit through a nozzle insert 6 (discussed in greater detail below) and out of a nozzle (not shown). Connected to the fluid conduit 5 around the nozzle insert 6 is a liquid conduit 7.

The liquid conduit 7 is made from a rigid or substantially rigid material such as a metal, alloy or plastics material, and is of a generally tubular construction to permit liquid to be transported therein. Although not shown, the open end 8 of the liquid conduit 7 is provided with a sharpened point or the like to assist the penetration of a wick 9 of a refill 10 of liquid.

The refill 10 is preferably a commercially available refill of liquid such as that sold under the brand AIRWICK® for use with a mains electric fragrance diffuser sold under the same brand. The refill 10 comprises a reservoir 11 that is partially or completely transparent thus allowing a user to monitor the liquid 12 level therein. The reservoir 11 is sealed with a plug (not shown) having an aperture therethrough, and the aperture is sized to correspond to the diameter or cross-section of the wick 9 to securely hold it in a fixed position whilst substantially maintaining a liquid seal to substantially or completely prevent the leaking of liquid from the reservoir.

The wick 9 may be made from any porous material wherein said porous material sufficiently malleable to permit the liquid conduit 7 to be at least partially inserted therein. As shown in FIG. 1, the liquid conduit 7 is provided in a length that is less than the length of the wick 9 to permit the liquid conduit 7 to extend partially into the wick 9.

Although not shown in detail in FIG. 1, but shown in more detail in FIG. 2, the nozzle insert 6 is configured to be held in place by the nozzle and extend therefrom along the interior of the fluid conduit 5. At a rearward portion 13 of the nozzle insert 6 a channel is provided which may be inwardly tapered toward a forward portion (i.e. toward the nozzle) thereof to, in use, further lower the pressure and increase the speed of air pumped therethrough. Forward of the inward taper may be provided a ejector constriction portion 14 and forward from said ejector constriction portion may be provided an expansion chamber 15. The liquid conduit 7 connects to the fluid conduit 5 in the ejector constriction 14 portion to be in fluid communication with the fluid conduit 5 and/or the nozzle insert 6 such that, in use, the decrease in pressure at the connection draws liquid up the liquid conduit 7 into the fluid conduit 5 and/or nozzle insert 6 before being carried by the pumped air flow out of the nozzle into the environment surrounding the device 1.

As shown in FIG. 1 the liquid conduit 7 extends from the fluid conduit 5 with a length that will permit the liquid conduit 7 to penetrate the wick 9 but not be sufficiently long to contact a base interior surface of the reservoir 11. This arrangement ensures that transport of the liquid 12 from the reservoir 11 is achieved by a combination of the liquid 12 being transported first by capillary action into the wick and subsequently transported via suction imposed by the ejector constriction acting in cooperation with the pumped air up into the liquid conduit 7 and out of the nozzle.

Although not illustrated, a device according to the second aspect of the present invention could be envisaged based on a multiplication of the features illustrated with reference to FIG. 1 and or with variations made thereto within the scope of ordinary skill in the art of making emanation devices.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An emanation device comprising:
   a replaceable refill of liquid containing one or more active materials wherein the active material comprises at least one of: a fragrance; an insecticide; a fungicide; a pesticide; a sanitising material; and/or a pharmaceutical; wherein the refill comprises a sealed reservoir containing said liquid and a porous wick made of a fibrous material and which extends from the interior of the reservoir to the exterior thereof; and wherein the device comprises:
   an air pump;
   a fluid conduit in fluid communication with the air pump such that, in use, air pumped by the pump will flow through the fluid conduit;
   a nozzle located at the end of the fluid conduit remote from the air pump;
   a ejector constriction provided in the fluid conduit adjacent or substantially adjacent the nozzle;
   a liquid conduit made of a rigid or substantially rigid material which is provided adjacent the ejector constriction and in fluid communication with the fluid conduit at one end thereof, and open at the other end to receive liquid therein;
   wherein the liquid conduit is located within the porous wick.

2. An emanation device according to claim 1, wherein the liquid conduit is made from a rigid or substantially rigid material and the open end of the liquid conduit is provided with a sharpened point.

3. An emanation device according to claim 1, wherein the liquid conduit is provided in a length that is less than the length of the wick.

4. An emanation device according to claim 1, wherein the wick is made from any porous material wherein said porous material sufficiently malleable to permit the liquid conduit to be at least partially inserted therein.

5. An emanation device according to claim 1, wherein the wick is sized to extend from a base of reservoir to protrude through a plug or a reservoir seal to extend thereabove.

6. An emanation device according to claim 1, wherein the device is adapted to retain the refill in a substantially fixed position relative to the device.

7. An emanation device according to claim 1, wherein the air pump is configured to pump air through the fluid conduit within a range of 0.4-1.0 liters/min.

8. An emanation device according to claim 1, wherein the ejector constriction is provided in the form of a nozzle insert.

9. An emanation device according to claim 8, wherein the nozzle insert is configured to extend from or adjacent the nozzle along the interior of the fluid conduit and is provided at a rearward portion thereof that is remote from the nozzle with a channel, and the channel is inwardly tapered toward a forward portion thereof to, in use, further lower the pressure and increase the speed of air pumped therethrough, and forward of the inward taper is provided a ejector constriction portion, and forward from said ejector constriction portion is provided an expansion chamber, wherein the liquid conduit connects to the fluid conduit in the ejector constriction portion to be in fluid communication with the fluid conduit and/or the nozzle insert such that, in use, the decrease in pressure at the connection draws liquid up the liquid conduit into the fluid conduit and/or nozzle insert before being carried by the pumped air flow out of the nozzle or nozzle insert into the environment surrounding the device.

10. An emanation device according to claim 1, wherein the ejector constriction is formed integrally with the fluid conduit adjacent the nozzle.

11. An emanation device according to claim 1, wherein the ejector constriction is formed integrally with the nozzle.

12. An emanation device according to claim 1, wherein the device is provided with a controller that is configured to control the air pump to control the spraying of liquid from the device.

13. An emanation device according to claim 12, wherein the controller is provided with a timer to permit the controller to instruct the pump to operate for periods defined by the controller.

14. An emanation device according to claim 13, wherein the device is provided with user input to allow a user to instruct the controller how long to spray for and/or how often to spray for and/or the spray rate of the device.

15. An emanation device according to claim 12, wherein the device is provided with a sensor which is connected to the controller wherein said sensor is configured to detect a characteristic in the environment surrounding the device, and wherein the controller is operative to analyse an input from the sensor and control the air pump to spray a determined amount of liquid.

16. An emanation device according to claim 15, wherein the sensor is at least one motion sensor and at least one odour sensor.

17. An emanation device according to claim 1, wherein the device is battery powered.

18. An emanation device according to claim 7, wherein the air pump is configured to pump air through the fluid conduit within a range of 0.6-0.8 liters/min.

19. A method of emanating a liquid containing one or more active materials wherein the active material comprises at least one of: a fragrance; an insecticide; a fungicide; a pesticide; a sanitising material; wherein said method comprises the steps of:
at least partially inserting a liquid conduit of an emanating device according to claim 1 into a wick of a refill of liquid containing one or more active materials;
causing an air pump to pump air into a fluid conduit and out of a nozzle past a ejector constriction such that liquid is sucked from the wick into the liquid conduit and out of the nozzle into the environment surrounding the device.

20. A fragrance emanation device adapted for use with a replaceable refill of liquid containing one or more active materials wherein the active material comprises at least one fragrance;
wherein the refill comprises a sealed reservoir containing said liquid and a porous wick made of a fibrous material and which extends from the interior of the reservoir to the exterior thereof wherein the device comprises:
an air pump;
a fluid conduit in fluid communication with the air pump such that, in use, air pumped by the pump will flow through the fluid conduit;
a nozzle located at the end of the fluid conduit remote from the air pump;
a ejector constriction provided in the fluid conduit adjacent or substantially adjacent the nozzle;
a liquid conduit made of a rigid or substantially rigid material which is provided adjacent the ejector constriction and in fluid communication with the fluid conduit at one end thereof, and open at the other end to receive liquid therein;
wherein the liquid conduit is located within the porous wick.

21. A fragrance emanation device adapted for use with two or more replaceable refills of liquid each containing one or more active materials wherein the active material comprises at least one fragrance;
wherein the refills each comprise a sealed reservoir containing said liquid and a porous wick made of a fibrous material and which extends from the interior of the reservoir to the exterior thereof wherein the device comprises:
one or more air pumps;
two or more fluid conduits corresponding to the number of replaceable refills, wherein said fluid conduits are in fluid communication with the or each air pump such that, in use, air pumped by the pump(s) will flow through the fluid conduits;
a nozzle located at the end of each fluid conduit remote from the air pump(s);
a ejector constriction provided in each fluid conduit adjacent or substantially adjacent the nozzle;
a liquid conduit made of a rigid or substantially rigid material which is provided adjacent each ejector constriction and in fluid communication with the respective fluid conduit at one end thereof, and open at the other end to receive liquid therein;
wherein each liquid conduit is located within respective porous wicks of said two or more replaceable refills.

22. An emanation device comprising:
two or more replaceable refills of liquid containing one or more active materials wherein the active material comprises at least one of: a fragrance; an insecticide; a fungicide; a pesticide; a sanitising material; and/or a pharmaceutical; wherein the refills each comprise a sealed reservoir containing said liquid and a porous wick made of a fibrous material and which extends from the interior of the reservoir to the exterior thereof; and wherein the device comprises:
one or more air pumps;
two or more fluid conduits corresponding to the number of replaceable refills, wherein said fluid conduits are in fluid communication with the or each air pump such that, in use, air pumped by the pump(s) will flow through the fluid conduits;

a nozzle located at the end of each fluid conduit remote from the air pump(s);
a ejector constriction provided in each fluid conduit adjacent or substantially adjacent the nozzle;
a liquid conduit made of a rigid or substantially rigid material which is provided adjacent each ejector constriction and in fluid communication with the respective fluid conduit at one end thereof, and open at the other end to receive liquid therein;
wherein each liquid conduit is located within respective porous wicks of said two or more replaceable refills.

\* \* \* \* \*